(12) United States Patent
Johnston et al.

(10) Patent No.: US 6,309,607 B1
(45) Date of Patent: Oct. 30, 2001

(54) SLIDE STAINING SYSTEM

(76) Inventors: Robert John Johnston, 44 Merrygreen Place, Stewarton Kilmarnck KA3 5EP; Ronald William Miller, 7 Kenbank Road, Bridge of Weir, Renfrew PA1 3AZ, both of (GB)

( * ) Notice: Subject to any disclaimer, the term of this patent is extended or adjusted under 35 U.S.C. 154(b) by 0 days.

(21) Appl. No.: 09/438,990
(22) Filed: Nov. 12, 1999
(51) Int. Cl.[7] ....................................... B01L 9/00
(52) U.S. Cl. ..................... 422/104; 422/300; 422/58; 118/423; 118/428; 118/500
(58) Field of Search ..................... 118/500, 503, 118/423, 428; 422/99, 104, 300, 58; 134/142, 149, 157–159, 165; 248/121, 122.1, 125.9; 269/37

(56) References Cited

U.S. PATENT DOCUMENTS

| | | | |
|---|---|---|---|
| 4,651,671 | * | 3/1987 | Pedersen ............................. 118/425 |
| 4,975,250 | * | 12/1990 | Mordecki ............................. 422/99 |
| 6,235,241 | * | 5/2001 | Catt et al. ............................. 422/56 |

* cited by examiner

Primary Examiner—Laura Edwards
(74) Attorney, Agent, or Firm—Ratner & Prestia

(57) ABSTRACT

A slide staining system has a slide holder assembly comprising a plurality of slide holders 3 each holding a slide 2. The holders are mounted rotatably with respect to each other and can rotate between a first position where all holders are aligned and a second position where each slide holder is offset by a predetermined angle from an adjacent slide holder.

19 Claims, 4 Drawing Sheets

SLIDE STAINING SYSTEM

FIELD OF THE INVENTION

This invention relates to a slide staining system, particularly an integrated slide based immunocytochemical staining system covering slide preparation, reagent application and removal, rinsing find drying for examination.

DESCRIPTION OF THE PRIOR ART

Present slide staining systems involve microscope slides being disposed horizontally along inserts at the base of a rectangular staining enclosure. These staining enclosures may be of plastic or metal construction. A small quantity of liquid is added to the box, which is subsequently covered. This forms the moist environment chamber where staining can take place each washing stage of a staining procedure necessitates removal of the slides to a vertical rack assembly and hence co a second vessel containing the wash fluid. Following washing, each slide is manually dried and replaced in the staining chamber. This is both time consuming and error prone. Alternative systems for specimen staining have been proposed These have not gained acceptance due to their high cost and requirement to adopt new procedures The object of the present invention is to offer a low cost, modular, integrated system for specimen processing which is designed to be complimentary with established and standard laboratory practice.

SUMMARY OF THE INVENTION

According to a first aspect of the present invention there is provided a slide holder assembly for holding a plurality of slides, said assembly comprising a plurality of individual slide holders, each slide holder being adapted to rotate about a common axis of rotation and comprising a mounting portion adapted to receive one end of a slide, the slide holders being mounted within said assembly in spaced arrangement along said common axis for rotation about said common axis, such that the slide holders can rotate between a first position where all the slide holders are substantially aligned in a direction parallel to said common axis and a second position where each slide holder is offset by a predetermined angle from the adjacent slide holder.

Preferably the slide holder assembly further comprises a shaft extending along the common axis. Most preferably the slide holder assembly further comprises a base having a support member, wherein shaft is hollow and adapted to engage over the support member.

Preferably each slide holder contains a substantially planar axial portion having a thickness greater than said mounting portion and having an aperture therein.

Preferably the axial portion of each slide holder is adapted to rotate in slidable contact with the axial portion of an adjacent slide holder.

Preferably each slide holder is provided with means to limit the relative rotation of the slide holder with an adjacent slide holder.

Preferably the axial portion is provided wish a projection on a first face of the axial portion and a corresponding circumferential slotted groove in a second opposite face of the axial portion, adapted to receive the projection in the first face of the axial portion of the adjacent slide holder.

Preferably the slotted groove is positioned such that when the projection in the first face of the axial portion of the adjacent slide holder abuts a first end of the groove the mounting portion of the slide holder is aligned with that of the adjacent slide holder.

Preferably the slotted groove is positioned such that when the projection in the first face of the axial portion of the adjacent slide holder abuts a second end of the groove the mounting portion of the slide holder is offset from that of the adjacent slide holder by a predetermined angle.

preferably the predetermined angle selected so be $360°/n$, where n is the number of slide holders. The predetermined angle may be $36°$ where the assembly comprises 10 slide holders.

According to a second aspect of the present invention there is provided a slide system comprising a slide holder assembly according to the first aspect and a wash tank. The wash tank is preferably adapted to receive the holder assembly such that in use the slides held by the mounting means are vertical.

Preferably the assembly comprises a shaft oriented on said common axis of rotation of said slide holders and a shaft housing.

Preferably said wash tank has one or more bearing surfaces configured to support one or more surfaces of said shaft housing.

Preferably the shaft housing comprises upper and lower cylindrical members connected to said shaft, the slide holders being mounted on said shaft between said upper and lower cylindrical members.

Preferably the wash tank comprises two opposing walls, each wall having at its upper end a part cylindrical nearing surface adapted to receive one of said upper and lower cylindrical members.

Preferably the slide system further comprises a lid for the wash tank, the lid comprising two opposing walls, each wall having at its lower end a part cylindrical bearing surface adapted to be located on one of said upper and lower cylindrical members.

Preferably there is provided a slide staining system comprising one or more of the following:

a slide holder assembly according to the first aspect;

one or more application stations;

an environmental (moist) chamber;

an aqueous/solvent wash bath;

a vacuum device for removal of excess fluid;

a stirrer unit; and a dryer unit.

DESCRIPTION OF THE PREFERRED EMBODIMENT

The preferred embodiment of the invention is described with reference to FIGS. 1 to 4. The slide staining system of the invention comprises a slide holder assembly (the figures show a version for 10 slides) which can optionally be used with one or more of the following: an application station, an environmental or moist chamber, aqueous/solvent wash baths, a stirrer unit and dryer units. A vacuum device for removal of excess fluid may also form part of the system.

Slide Holder Assembly

Figure 1:
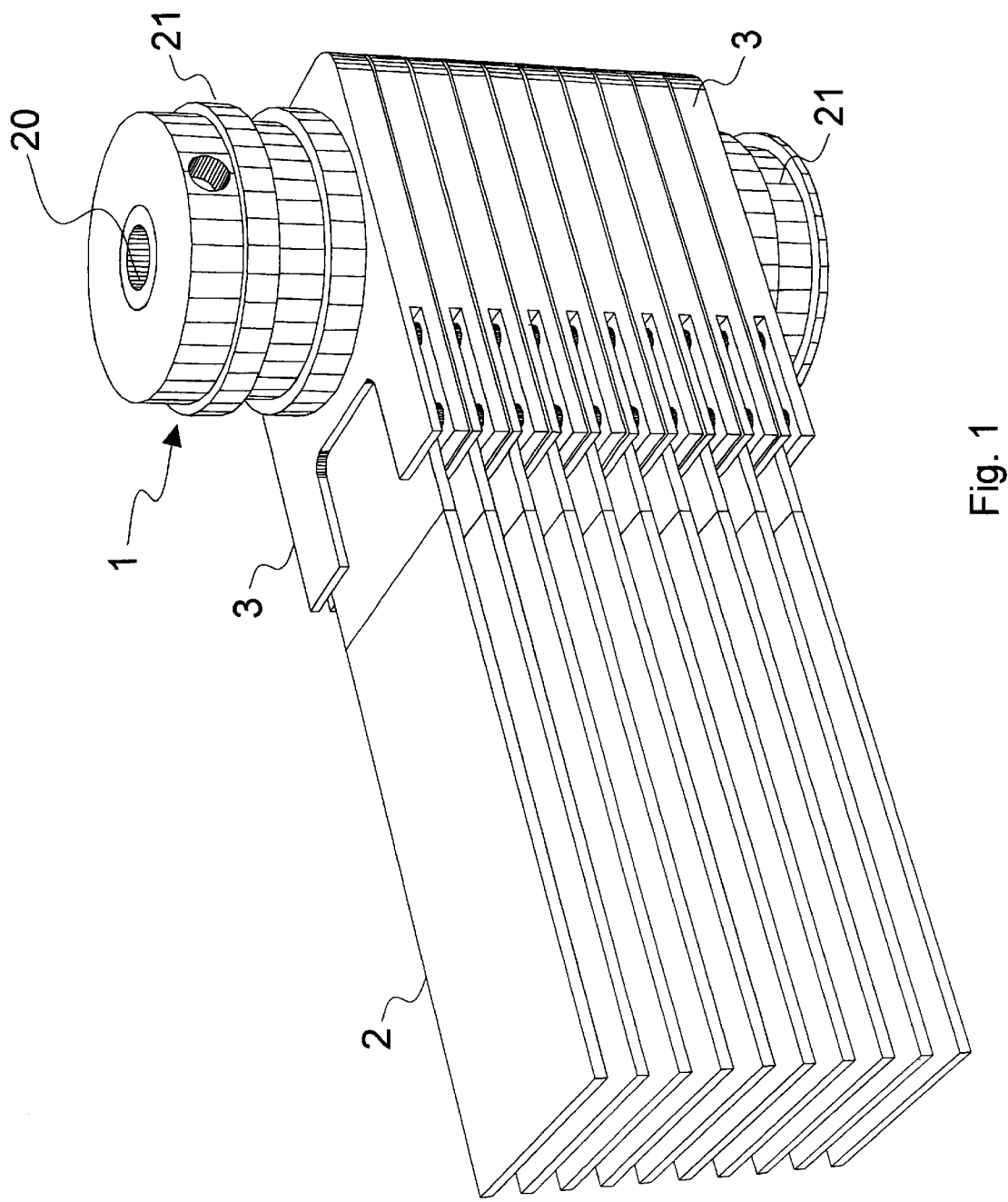
FIG. 1 illustrates a elide holder assembly according to the invention.

FIG. 1 shows a slide holder assembly 1. This unit is constructed totally from plastic components to permit use within a microwave-heating unit. Slides 2 are secured firmly at one end within individual holders 3 that are linked in such a way that the holders may be rotated relative to each other within the plane of the slide. The slide holders 3 themselves may be fitted with a recess (not shown) for the fitting of a coloured tab or insert to indicate status.

Figure 2:
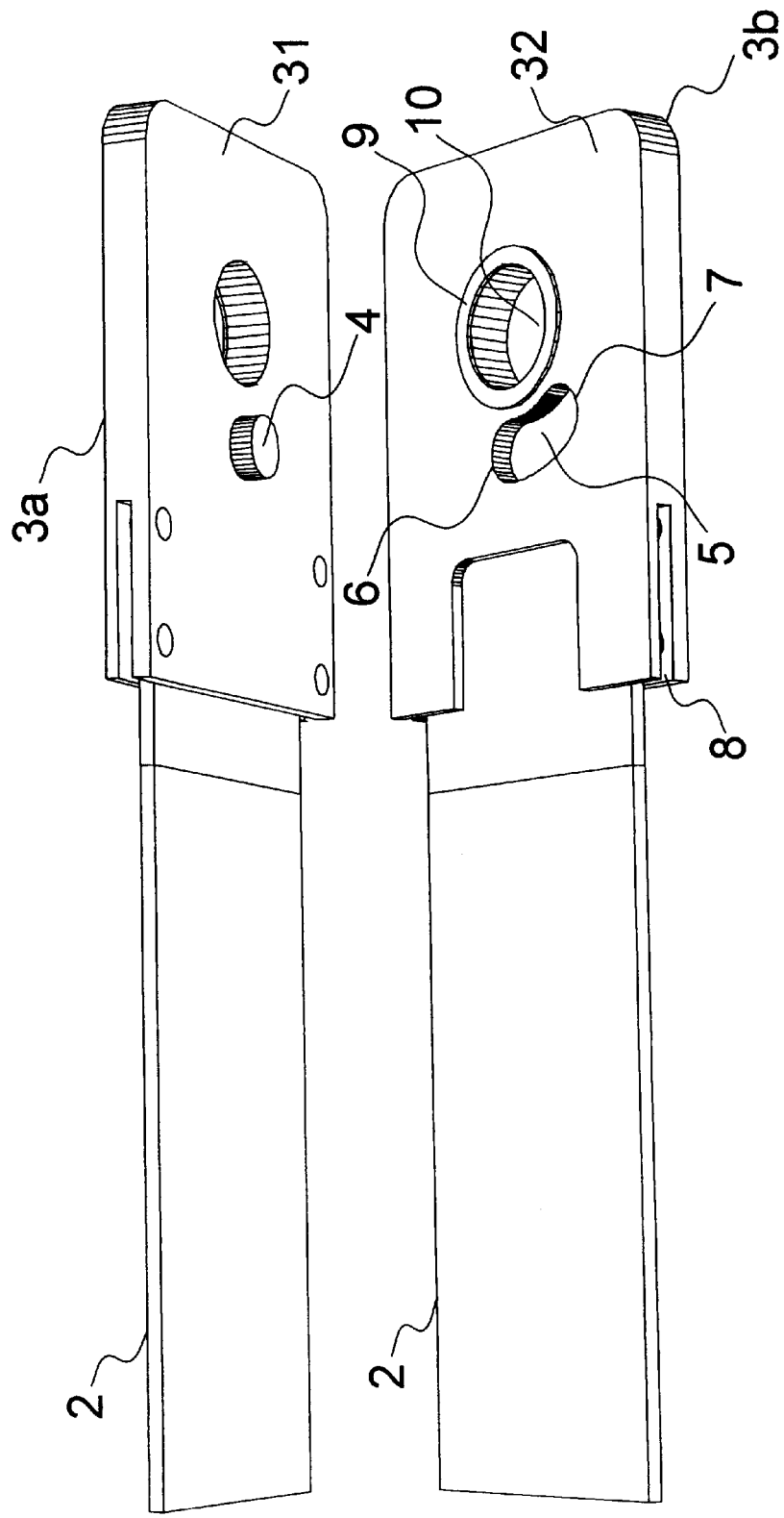
FIG. 2 illustrates a slide holder of the assembly of FIG. 1.

The holders are inter-linked in such a way that the slides can fan out to cover one complete rotation. In other words, each slide holder is offset by an angle of 36 ° relative to the adjacent slide holder. The method of inter-linking is illustrated in FIG. 2, which shows the lower side 31 of a first slide holder 3a and the upper side 32 of a second slide holder 3b. The lower side 31 has a small cylindrical projection or lug 4 which is positioned so as to locate in an arcuate groove 5. When the lug 4 contacts the first end 6 of the slotted groove 5, the two slide holders 3a and 3b are mutually aligned with each other. When the lug 4 contacts the second end 7 of the slotted groove 5, the two slide holders are at a predetermined angle to each other. In the illustrated example using ten slide holders the predetermined angle is 36°, but it is to be understood that other angles are possible. In order to fan the slides 2 out it is necessary only co rotate the top slide or slide holder, and the resultant rotation of the lug 4 will cause the next slide holder to rotate when the lug 4 meets the end 7 of the slot, and in turn causing all of the slide holders 3 to rotate with respect to each other.

Each slide holder has a slotted mounting portion 8 for receiving a standard slide, as well as a ring-like axial portion 9 with a circular aperture 10. The axial portion 9 has a thickness greater than that of the slide holder body, so that it is only the axial portions 9 of adjacent slide holders which are in mutual contact. The upper and lower surfaces of the axial portion 9 are planer and parallel, to allow smooth sliding of adjacent surfaces when the slide holders are rotated.

In the illustrated embodiment a hollow shaft 20 extends through the aperture 10 of each slide holder. The shaft is supported at its ends by cylindrical members 21 which serve to house the shaft 20. However it is to be understood that each slide holder may be provided with means to engage the adjacent slide holder, for example a circular annulus (not shown) around the aperture 10 on the lower face 31 of the slide holder which engages with the ring-like portion of the axial portion 9 which extends above the upper face 30 of the adjacent slide holder. In such circumstances the shaft 20 may be omitted.

Wash Bath Unit

Figure 4:
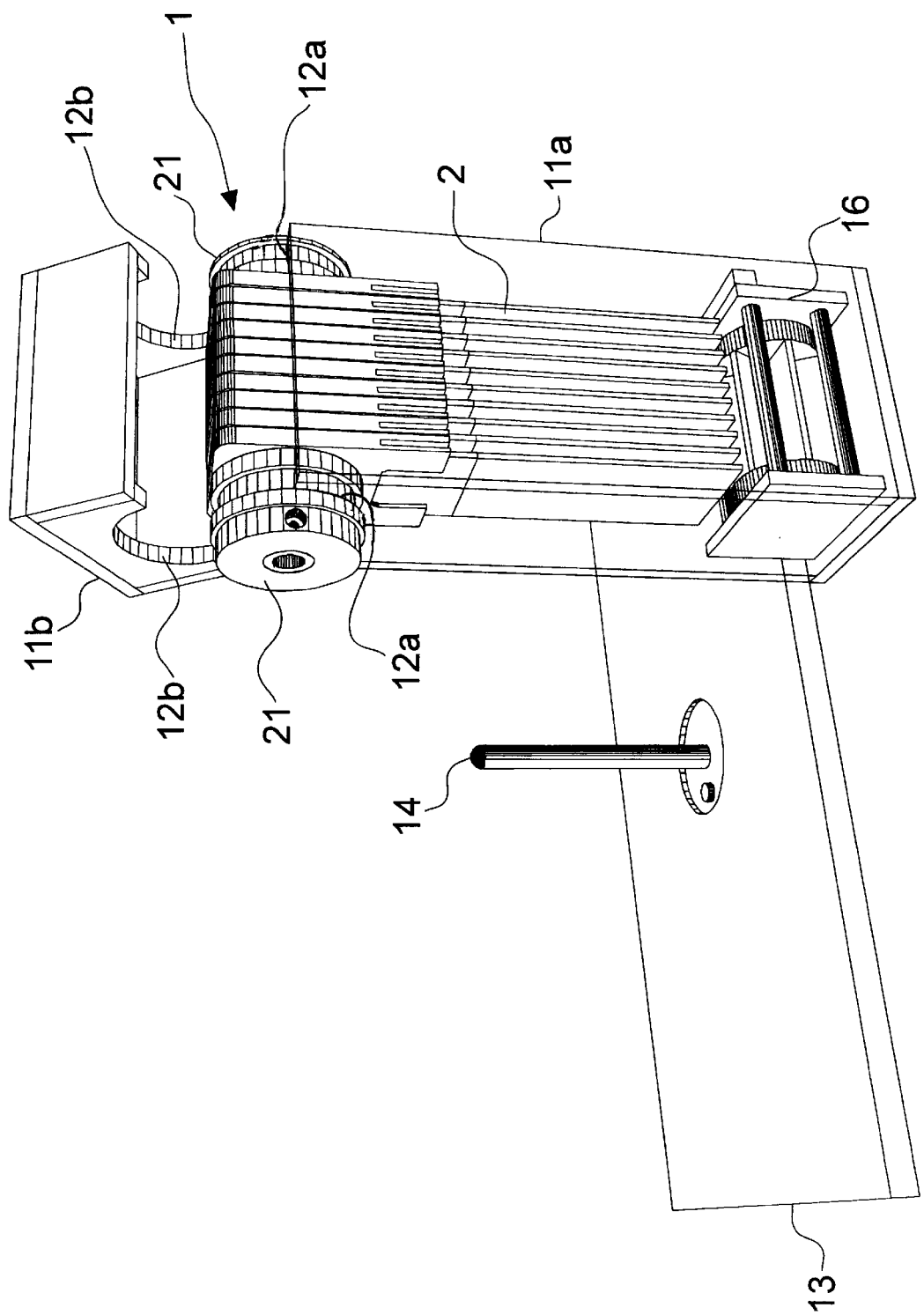
FIG. 4 illustrates a wash bath with stirrer together with a slide holder assembly according to the invention.

FIG. 4 shows an open topped rectangular section bath 11a with the top section designed to accommodate the slide holder unit 1 such that the slides 2 are suspended vertically within the fluid contained in the bath 11a. The unit may be fitted with a lid 11b. Both the bath 11a and lid 11b have semi-circular recesses 12a, 12b in their side walls which fit around the shaft housings 21. The material chosen for the unit is preferably transparent or translucent and resistant to solvents such as xylene and ethanol. The unit is preferably tall enough to accommodate a stirrer unit 16 in the rank base beneath the slides which will improve the efficiency of washing.

Application Station

The application station consists of a base plate 13 and incorporates a stand or pin 14 that passes through the pivot end of the slide holder. The stand 14 engages the hollow cylindrical shaft 20 of the slide holder assembly 1.

The slides can then be fanned out from this point, either to 360 degrees to allow access to all 10 slides or to 36 degrees to allow access to one slide at a time for the application of small volumes of reagent.

A light source (not shown) may be built in to the application station to allow visualisation of the area of interest on the slide.

Moist Chamber

Figure 3:
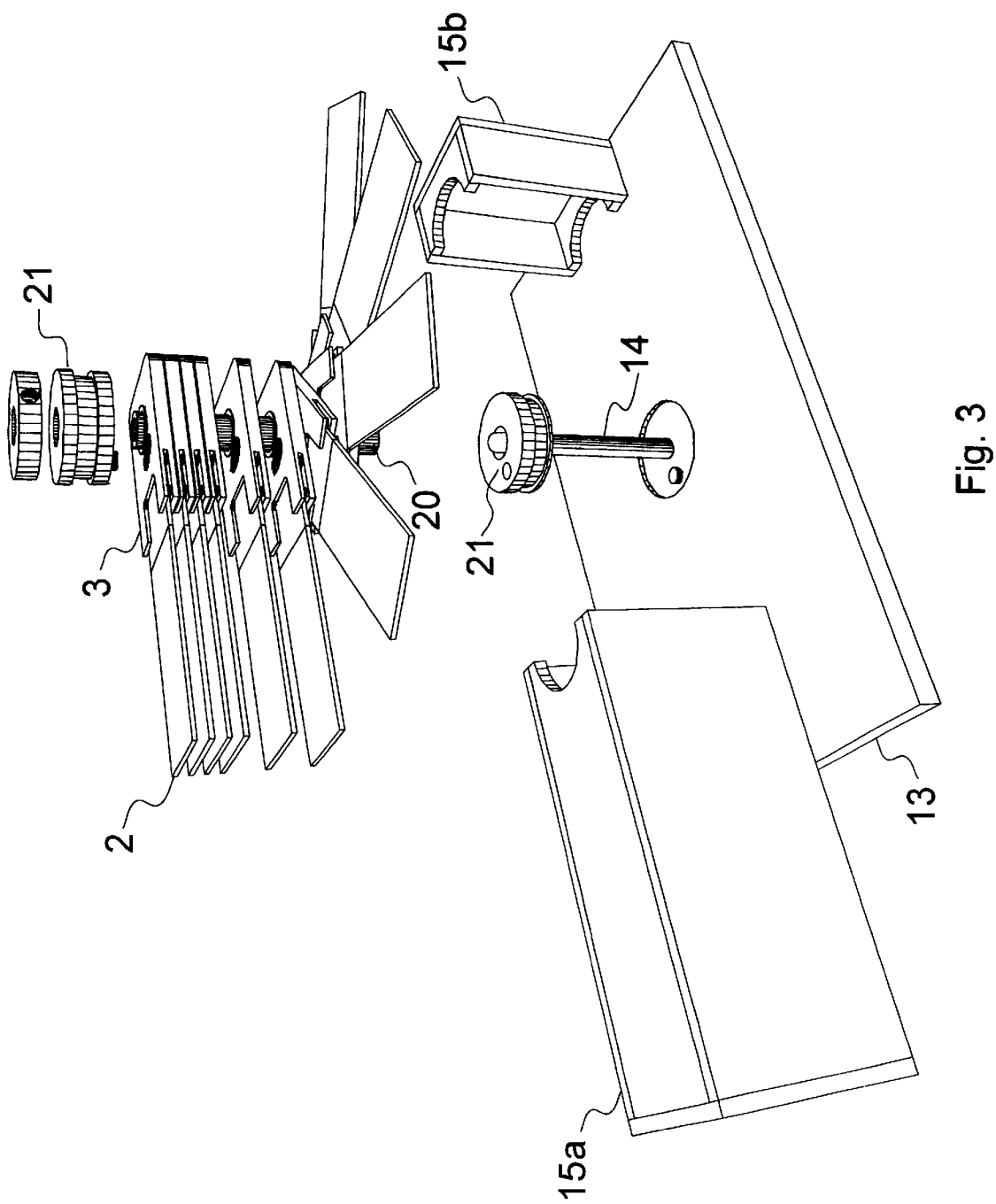
FIG. 3 illustrates an application station and environmental (moist) chamber together with a slide holder assembly according to the invention.

FIG. 3 illustrates the moist chamber, comprising a main unit 15a together with lid 15b. The moist chamber may be similar in construction to the wash bath unit, and semi-circular recesses 15c enable the moist chamber 15a and lid 15b to fit sealingly around the shaft housings 21, so that the moist chamber is effectively closed off. The purpose of this unit is to allow slides to be incubated in the horizontal position while preventing drying out of the small volumes of reagent normally used in immunocytochemistry.

Dryer Unit

The dryer unit (not illustrated) may be provided as a separate chamber. It is used to accelerate the removal of residual moisture from the processed specimens prior to examination. This may be accomplished by applying controlled heat to the lower surface of the slide while passing a low volume of air over the upper surface. It may be similar in appearance to the moist chamber 15a, 15b.

Stirrer

The stirrer unit 16 illustrated in FIG. 4 consists of a paddle blade unit driven by an external motor unit (not shown) via a magnetic coupling. It is possible to drive several stirrer assemblies from one motor unit. The stirrer unit is placed in the bottom of the wash tank 11a.

In operation the system is designed to enable the processing of standard glass microscope slides supporting specimens of biological material such a tissue sections, smears or aspirates. The specimen is taken through processes such as de-waxing, rinsing, small volume reagent incubations, microwave treatment, elevated temperature incubation, washing and drying.

The power requirements of the system are furnished by a combination of mains AC power where appropriate and battery DC power where demanded on grounds of safety or convenience.

LCD display timer units may be fitted to the incubation units and optionally to the wash baths. These are powered by built-in battery sources and support count down and memory recall functions. The timer start, stop, set and recall functions may be controlled by a set of moisture proof push-button switch units. Lighting built in to the application unit may be controlled by a moisture proof latching push-button control. Electric motor drives for stirrer units may be controlled by moisture proof rocker type switch units.

Timer alarms may be both audible and visible. Visible indication of electrical mains power connection may be provided.

Units powered by mains electricity may be connected by IEC type fused plug power supply cables connecting to double IEC inlet sockets on the equipment.

System maintenance is low and easily carried out by the user. The following is a typical maintenance schedule:
 a) Inspection of electrical cable and plug condition.
 b) Routine cleaning and inspection of tank units for leakage.
 c) Inspection of slide holder clips for breakage/cracking.
 d) Check for correct operation of timer units.
 e) Inspection of battery condition.

The system can be operated manually, but there exists the possibility to automate operation. Automatic functions may include automatic slide loading, using established servo/stepper motor technology; automatic reagent application via motor controlled applicator assemblies, automatic protocol stage sequencing and automatic timing and environmental control.

What is claimed is:

1. A slide holder assembly for holding a plurality of slides, said assembly comprising a plurality of individual slide holders, each slide holder being adapted to rotate about a common axis of rotation and comprising a mounting portion adapted to receive one end of a slide, the slide holders being mounted in spaced arrangement along said common axis for rotation about said common axis, such that the slide holders can rotate between a first position where all the slide holders are substantially aligned in a direction parallel to said common axis and a second position where each slide holder is offset by a predetermined angle from an adjacent slide holder.

2. The slide holder assembly of claim 1, further comprising a shaft extending along the common axis.

3. The slide holder assembly of claim 2, further comprising a base having a support member, wherein the shaft is hollow and is adapted to engage over the support member.

4. The slide holder assembly of claim 1, wherein each slide holder contains a substantially planar axial portion having a thickness greater than said mounting portion and having an aperture therein.

5. The slide holder assembly of claim 4, wherein the axial portion of each slide holder is adapted to rotate in slidable contact with the axial portion of the adjacent one of said slide holders.

6. The slide holder assembly of claim 4, wherein each slide holder is provided with means to limit the relative rotation of the slide holder with the adjacent one of said slide holders.

7. The slide holder assembly of claim 6, wherein the axial portion of each slide holder has first and second opposing faces and is provided with a projection on the first face and a corresponding circumferential slotted groove in the second face adapted to receive the projection on the first face of an adjacent one of said slide holder.

8. The slide holder assembly of claim 7, wherein the slotted groove in each slide holder has a first end and a second end and wherein the slotted groove in each slide holder is positioned such that when the projection in the first face of the adjacent one of said slide holders abuts the first end of the groove the mounting portion of the slide holder is aligned with the mounting portion of the adjacent one of said slide holders.

9. The slide holder assembly of claim 8, wherein said slotted groove in each slide holder is positioned such that when the projection in the first face of the adjacent one of said slide holders abuts the second end of the groove the mounting portion of the slide holder is offset from the mounting portion of the adjacent one of said slide holders by said predetermined angle.

10. The slide holder assembly of claim 1, wherein the predetermined angle is selected to be $360°/n$, where n is the number of slide holders.

11. A slide staining system comprising a slide holder assembly according to claim 1 and a wash tank.

12. The slide staining system of claim 11, wherein the slide holder assembly comprises a shaft extending along the common axis, said shaft being housed in a shaft housing.

13. The slide staining system of claim 12, wherein said wash tank has one or more bearing surfaces supporting one or more surfaces of said shaft housing.

14. The slide staining system of claim 13, wherein the shaft housing comprises upper and lower cylindrical members connected to said shaft, the slide holders being mounted on said shaft between said upper and lower cylindrical members.

15. The slide staining system of claim 14, wherein the wash tank comprises two opposing walls, each wall having at its upper end a part cylindrical bearing surface adapted to receive one of said upper and lower cylindrical members.

16. The slide staining system of claim 15, wherein the slide system further comprises a lid for the wash tank, the lid comprising two opposing walls, each wall having at its lower end a part cylindrical bearing surface adapted to be located on one of said upper and lower cylindrical members.

17. A slide staining system comprising a slide holder assembly for holding a plurality of slides, said assembly comprising a plurality of substantially planar slide holders rotatably mounted on a hollow shaft extending substantially perpendicular to the planar slide holders, each slide holder comprising a mounting portion adapted to receive one end of a slide, the slide holders being mounted in spaced arrangement along said hollow shaft, such that the slide holders can rotate between a first position where all the slide holders are substantially mutually aligned in a direction parallel to the axis of said hollow shaft and a second position where each slide holder is offset by a predetermined angle from an adjacent slide holder, the slide staining system further comprising a substantially planar base member and a pin member extending perpendicular to the base member, the hollow shaft being removably engageable with the pin member.

18. The slide staining system of claim 7, further comprising a wash bath comprising a base and side walls, said side walls being provided with support means to support said slide holder assembly such that in use the slide holders may be suspended vertically in the wash bath when the slide holders are mutually aligned.

19. The slide staining system of claim 7, further comprising a moist chamber comprising main portion and a lid portion adapted to fit sealingly around said slide holder assembly.

* * * * *